United States Patent
O'Connor

(10) Patent No.: US 8,114,466 B2
(45) Date of Patent: Feb. 14, 2012

(54) METHODS OF APPLYING COATING TO THE INSIDE SURFACE OF A STENT

(75) Inventor: Timothy O'Connor, Claregalway (IE)

(73) Assignee: Boston Scientific Scimed, Inc., Maple Grove, MN (US)

(*) Notice: Subject to any disclaimer, the term of this patent is extended or adjusted under 35 U.S.C. 154(b) by 973 days.

(21) Appl. No.: 11/968,828

(22) Filed: Jan. 3, 2008

(65) Prior Publication Data

US 2008/0213464 A1 Sep. 4, 2008

Related U.S. Application Data

(60) Provisional application No. 60/878,074, filed on Jan. 3, 2007.

(51) Int. Cl.
*A61L 33/00* (2006.01)

(52) U.S. Cl. ............ 427/2.25; 536/123.1; 606/193; 427/2.24; 427/230; 427/231; 427/232; 427/233; 427/234; 427/239; 427/421.1; 427/424; 427/425; 427/427.1; 427/427.2; 427/427.3; 427/427.4; 427/427.5

(58) Field of Classification Search .......... 536/123.1; 606/194; 427/2.25

See application file for complete search history.

(56) References Cited

U.S. PATENT DOCUMENTS

| | | | |
|---|---|---|---|
| 3,983,581 A | 10/1976 | Angell et al. | |
| 4,035,849 A | 7/1977 | Angell et al. | |
| 4,295,444 A | 10/1981 | Hatta et al. | |
| 5,091,205 A | 2/1992 | Fan | |
| 6,156,373 A | 12/2000 | Zhong et al. | |
| 6,174,329 B1 | 1/2001 | Callol et al. | |
| 6,190,404 B1 | 2/2001 | Palmaz et al. | |
| 6,322,847 B1 | 11/2001 | Zhong et al. | |
| 6,364,893 B1* | 4/2002 | Sahatjian et al. | ............ 606/194 |

(Continued)

FOREIGN PATENT DOCUMENTS

WO 03037223 A1 5/2003

(Continued)

*Primary Examiner* — Dah-Wei Yuan
*Assistant Examiner* — Andrew Bowman
(74) *Attorney, Agent, or Firm* — Kenyon & Kenyon LLP

(57) ABSTRACT

A method of applying a coating material to a stent includes the steps of providing a generally tubular stent having an inside surface and an outside surface and applying a coating material to the inside surface of the stent without applying that coating material to the outside surface of the stent. The method may comprise providing a mandrel having a diameter less than an interior diameter of the stent, providing the coating material around the mandrel, placing the stent around the mandrel and crimping the stent so that the inside surface of the stent contacts the coating material. Alternatively, the method may comprise providing an expandable device, providing the expandable device with the coating material such that the coating material is deliverable from the expandable device, placing the stent around the expandable device and expanding the expandable device such that the expandable device contacts the inside surface of the stent. Alternatively, the method may comprise providing an elongated material that is capable of having its diameter reduced under the application of a tensile force, providing the coating material around the elongated material, applying a tensile force to the elongated material, placing the stent around the elongated material and reducing or releasing the tensile force, thereby allowing the diameter of the elongated member to increase so that the coating material contacts the inside surface of the stent. The coating material may comprise an endothelial cell growth promoter.

15 Claims, 4 Drawing Sheets

U.S. PATENT DOCUMENTS

| | | |
|---|---|---|
| 6,517,888 B1 | 2/2003 | Weber |
| 6,613,897 B1 * | 9/2003 | Yatsuka et al. ............ 536/123.1 |
| 6,660,034 B1 | 12/2003 | Mandrusov et al. |
| 6,669,980 B2 | 12/2003 | Hansen |
| 6,743,463 B2 | 6/2004 | Weber et al. |
| 6,764,709 B2 | 7/2004 | Flanagan |
| 6,864,088 B2 | 3/2005 | Chen et al. |
| 6,899,731 B2 | 5/2005 | Li et al. |
| 6,939,320 B2 | 9/2005 | Lennox |
| 6,979,473 B2 | 12/2005 | O'Connor et al. |
| 6,984,411 B2 | 1/2006 | Palasis et al. |
| 7,008,411 B1 | 3/2006 | Mandrusov et al. |
| 7,482,034 B2 | 1/2009 | Boulais |
| 2004/0213893 A1 | 10/2004 | Boulais |
| 2005/0192662 A1 | 9/2005 | Ward |
| 2006/0251794 A1 | 11/2006 | Scheuermann |
| 2007/0141232 A1 | 6/2007 | Tochterman et al. |
| 2007/0259116 A1 | 11/2007 | Nolan et al. |

FOREIGN PATENT DOCUMENTS

| | | |
|---|---|---|
| WO | 2005034805 A1 | 4/2005 |

* cited by examiner

METHODS OF APPLYING COATING TO THE INSIDE SURFACE OF A STENT

RELATED APPLICATIONS

This application claims benefit of U.S. Provisional Application No. 60/878,074, filed Jan. 3, 2007, which is incorporated herein in its entirety.

TECHNICAL FIELD

The present invention generally relates to coated stents and methods of making such stents.

BACKGROUND

Various stents are known in the art, including both uncoated and coated stents. Prior art processes for coating stents include tumble coating, dip coating, spray coating, and electrostatic spraying. Because stents are typically formed as a lattice of struts or wire or some other open framework, during the coating methods listed above the coating gets applied to all exposed surfaces of the stent, including the surfaces that face toward the outside of the stent and the surfaces that face toward the inside of the stent.

Some examples of stents and processes for coating stents are shown and described in U.S. Pat. Nos. 6,669,980, 6,743,463, 6,979,473, 6,984,411, and U.S. Patent Application No. 20050192662, the disclosures of which are hereby incorporated by reference.

BRIEF DISCUSSION OF THE INVENTION

The present invention is directed to methods of applying coating to the inside surface of a stent.

In an embodiment of the invention, a method is provided for applying a coating material to a stent, comprising the steps of: (i) providing a generally tubular stent having an inside surface and an outside surface; (ii) providing a coating material; and (iii) applying the coating material to the inside surface of the stent without applying that coating material to the outside surface of the stent.

Applying a particular coating to the inside surface but not the outside surface provides the benefit of targeting the coating to where it is needed. For example, it is desirable to have a thin layer of endothelial cells grow over the struts or wires of an implanted stent as soon as possible after implantation to reduce the risk of restenosis and/or smooth muscle cell proliferation. An endothelial cell growth promoter such as vascular endothelial growth factor (VEGF) can be used to accelerate the growth of endothelial cells. In an embodiment of the invention, a stent has a coating comprising endothelial cell growth promoter on its inside surface (i.e., the surface that faces the interior of the lumen or cavity upon implantation). This is advantageous because the inside surface of the implanted stent is the area where it may be desired to have prompt cell coverage.

In an embodiment of the invention, a coating is applied to the inside surface of a stent by a diameter reduction process. A mandrel is provided with a transfer film or surface on which the desired coating is applied. The stent is placed over that mandrel and the diameter of the stent is reduced to contact the coating. The coating transfers to the inside surface of the stent. Heat can be applied to facilitate the coating transfer.

In another embodiment of the invention, a stent is loaded on an inflatable or expandable mandrel or balloon which has a transfer film or surface having the desired coating. The mandrel or balloon is then expanded to contact the inside surface of the stent, and the coating is transferred to the inside surface of the stent. In a specific embodiment, a balloon is used with a porous outer layer which becomes permeable and releases the coating upon reaching a specific pressure. A tube or mesh may be placed around the stent to prevent it from undesirably expanding. Heat can be applied to facilitate the coating transfer.

In another embodiment of the invention, an elongated material that reduces in diameter when placed under tensile force (such as SUPERFLOSS™ or elastic beading) carries the desired coating to be transferred to the inside surface of a stent. A tensile force is applied to the elongated material to stretch it, and a stent is loaded onto it. Then, the tensile force is reduced or released, allowing the diameter to expand, whereby the elongated material contacts the inside surface of the stent. The coating is transferred to the inside surface of the stent, which may be aided by moving the elongated material or the stent from side to side. Heat can be applied to facilitate the coating transfer.

BRIEF DESCRIPTION OF THE DRAWINGS

Referring to the drawings which form a part of this disclosure.

DETAILED DESCRIPTION OF THE ILLUSTRATED EMBODIMENTS

The illustrated embodiments show methods of coating the inside surface of a stent, i.e., the surface that faces the interior of the lumen or cavity upon implantation. As mentioned above, having a stent with a coating on the inside surface but not the outside surface is advantageous in certain situations, for example, for promoting endothelial cell growth on the inside surface of the stent through use of a coating material comprising an endothelial cell growth promoter.

Figure 6:
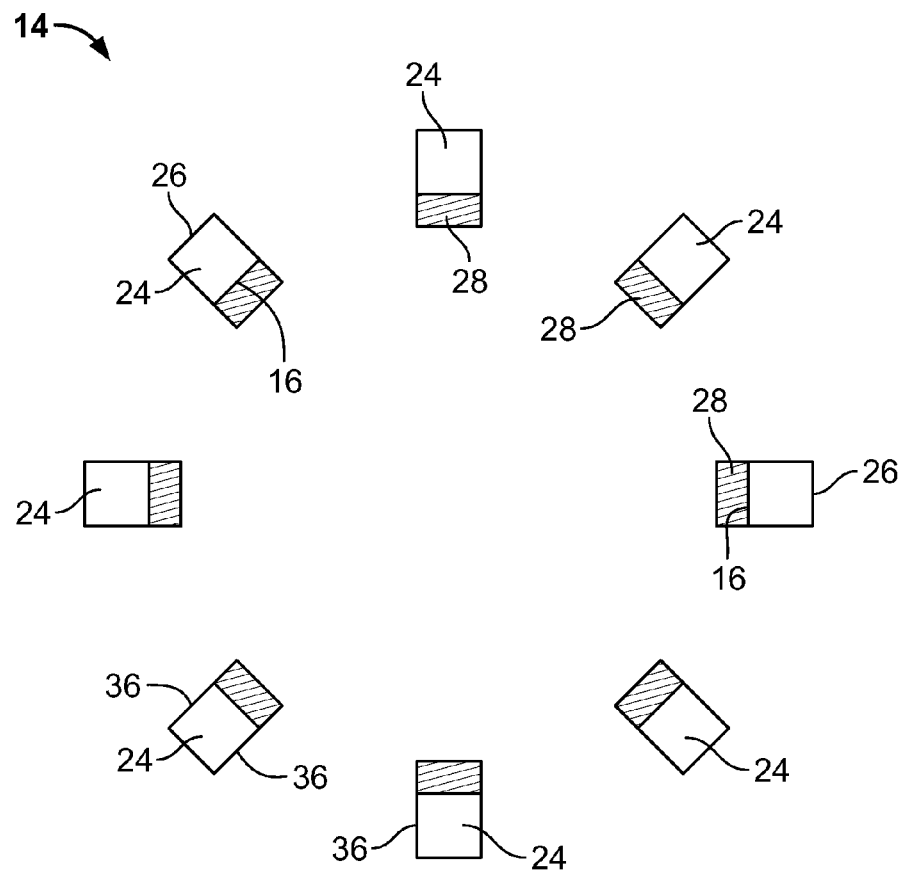
FIG. 6 shows a cross-sectional view of a stent with a coating that is on its inside surface but not on its outside surface.

FIG. 6 shows a cross-sectional view of a stent 14, showing the stent 14 as a series of struts 24. As can be seen in other figures, the stent 14 comprises a generally tubular base structure, the struts 24 of which are visible in FIG. 6. The stent 14 has an inside surface 16 and an outside surface 26. As illustrated in FIG. 6, the stent 14 has a coating 28 adhered to its inside surface 16 but not to its outside surface 26.

It will be appreciated that the invention described herein can be practiced in a variety of different ways. For example, in addition to the coating 28 on its inside surface 16, the stent 14 could have an additional coating on all of its surfaces. This additional coating could be applied before the coating 28, such that the coating 28 on the inside surface 16 of the stent overlies this additional coating. In such an embodiment, it should be understood that the base structure to which the coating of the invention is applied includes the underlying stent material and any coating, such that it is not necessary that the coating of the invention be adhered directly to the underlying stent material.

As shown in FIG. 6, the stent struts 24 may have lateral faces (or side or cut faces) 36. In certain embodiments, the coating 28 may overlie these lateral faces as well, but that is optional.

In the case of a stent made of wire having, for example, a round cross-section, it will be appreciated that a cross-section through the wire will not show clearly defined faces. In such a stent, the portions of the wire or stent material that generally face the interior of the lumen or cavity upon implantation comprise the inside surface of the stent, and the portions of the wire or stent material that generally face to the outside (e.g., to the tissue) comprise the outside surface of the stent. That is, it is not necessary for the stent to have clearly demarcated surfaces to practice the invention, so long as it is understood that the portions that generally face the inside comprise the inside surface and the portions that generally face the outside comprise the outside surface.

FIGS. 1 to 4 illustrate one embodiment of a method for applying a coating to the inside surface of a stent without applying that coating to the outside surface of the stent. In this embodiment, a mandrel 10 is provided with a transfer film 12 on which the desired coating material is carried. The coating material may be impregnated in or applied on the transfer film 12. The transfer film 12 may be, for example, Mylar, metal foil, or any other suitable material, having the desired coating material on one side. The transfer film 12 is placed around the mandrel 10 with the coating material facing out. The transfer film 12 may be a sheet that is wrapped around the mandrel or a sleeve. Alternatively, the apparatus may be used without a transfer film 12, in which case the coating material is directly on the surface of the mandrel 10. In either case, the coating material is provided around the mandrel.

Figure 1:
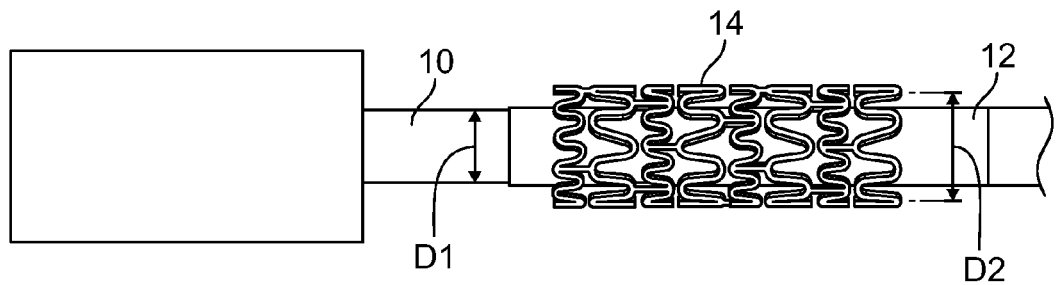
FIG. 1 shows a stent placed over a mandrel with a transfer film on the mandrel.

As can be seen in FIG. 1, in the initial condition, the mandrel 10 has a diameter D1 less than an interior diameter D2 of the stent 14. The stent 14 is placed over and around the mandrel 10 in the area of the coating material.

Figure 2:
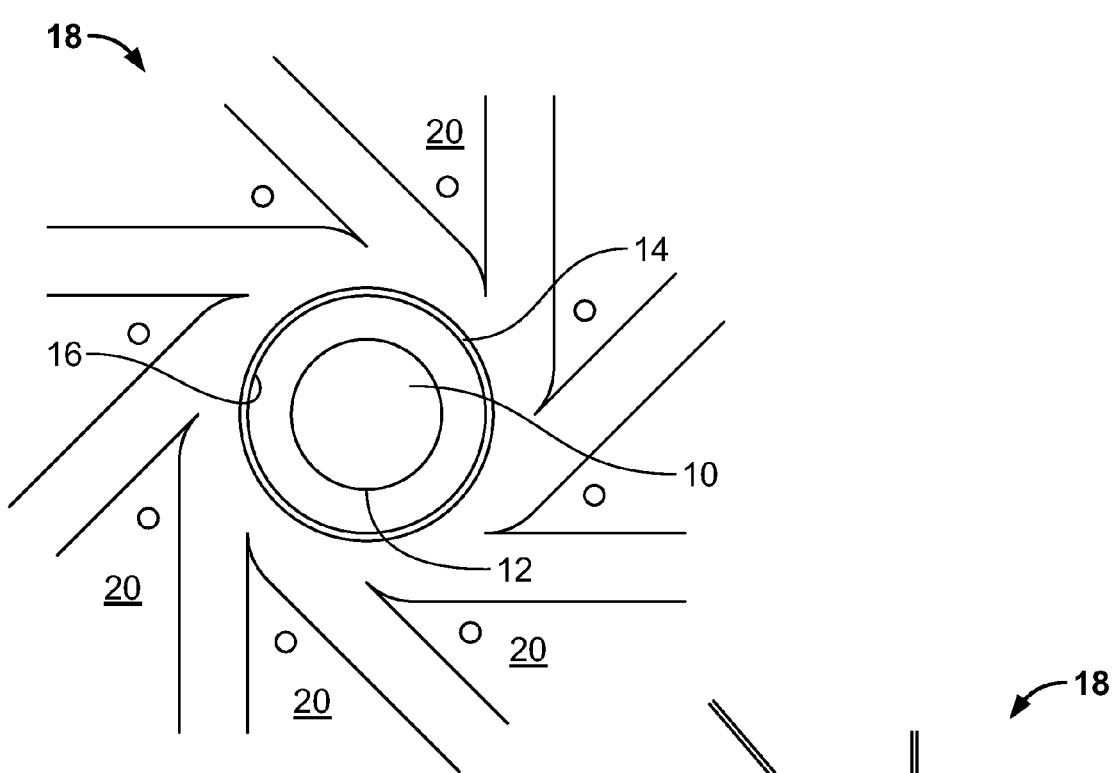
FIG. 2 shows a mechanism for crimping the stent on the mandrel of FIG. 1.
Figure 3:
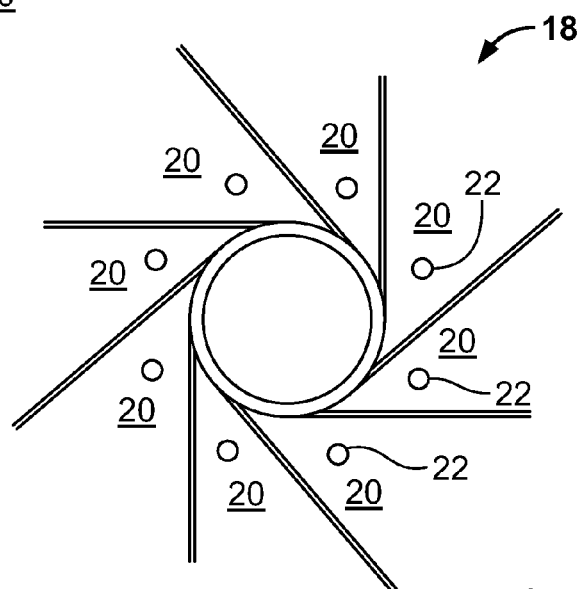
FIG. 3 shows the mechanism of FIG. 2 crimping the stent to a reduced diameter on the mandrel of FIG. 1.

FIG. 2 illustrates a mechanism 18 for reducing the diameter of, or crimping, the stent 14 so that the inside surface 16 of the stent 14 contacts the coating material on the film 12 or mandrel 10. The crimping mechanism 18 has a series of crimping jaws 20. As shown in FIG. 3, the crimping jaws close down on the stent 14 to reduce the diameter of the stent 14 and press the inside surface 16 of the stent down onto the coating material on the film 12 or mandrel 10. This causes the coating material to transfer from the film 12 or mandrel 10 to the inside surface 16 of the stent 14.

The crimping mechanism of FIGS. 2 and 3 may be similar to existing crimping mechanisms used for pre-reduction of a stent or for crimping of a stent onto a catheter. Pre-reduction is a process step that takes place before a stent is crimped onto a catheter and is used to reduce stent diameter, improve strut distribution and/or generally straighten the stent before a coating process or before loading the stent onto a catheter.

To facilitate the transfer of the coating material to the inside surface of the stent, heat can be applied. Heat can be applied by means of RF or microwave energy. The crimping jaws 20 may have heating elements or cartridges 22 that heat the crimping jaws 20 and thereby heat the stent 14. Additionally or alternatively, the mandrel 10 may be heated to assist the transfer of the coating material. This is analogous to a hot-stamp printing process.

Figure 4:
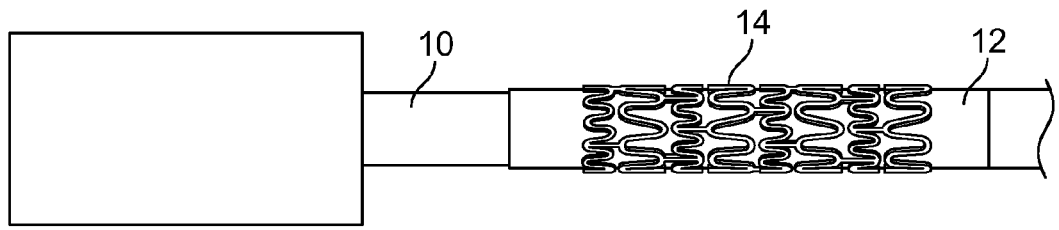
FIG. 4 shows the stent of FIG. 1 after being crimped on the mandrel.

FIG. 4 shows the stent 14 in its crimped state on the mandrel 10 and film 12. It will be understood that the stent 14 is held in this position by the crimping mechanism 18, although for clarity of illustration, the crimping mechanism 18 is not shown in FIG. 4. After the coating material has been transferred to the inside surface 16 of the stent 14, the pressure on the stent 14 from the crimping mechanism 18 is released. When this occurs, the stent 14 recoils slightly to a slightly larger diameter (because some of the deformation of the stent was in the elastic range). This facilitates removal of the coated stent 14 from the mandrel 10.

Figure 5:
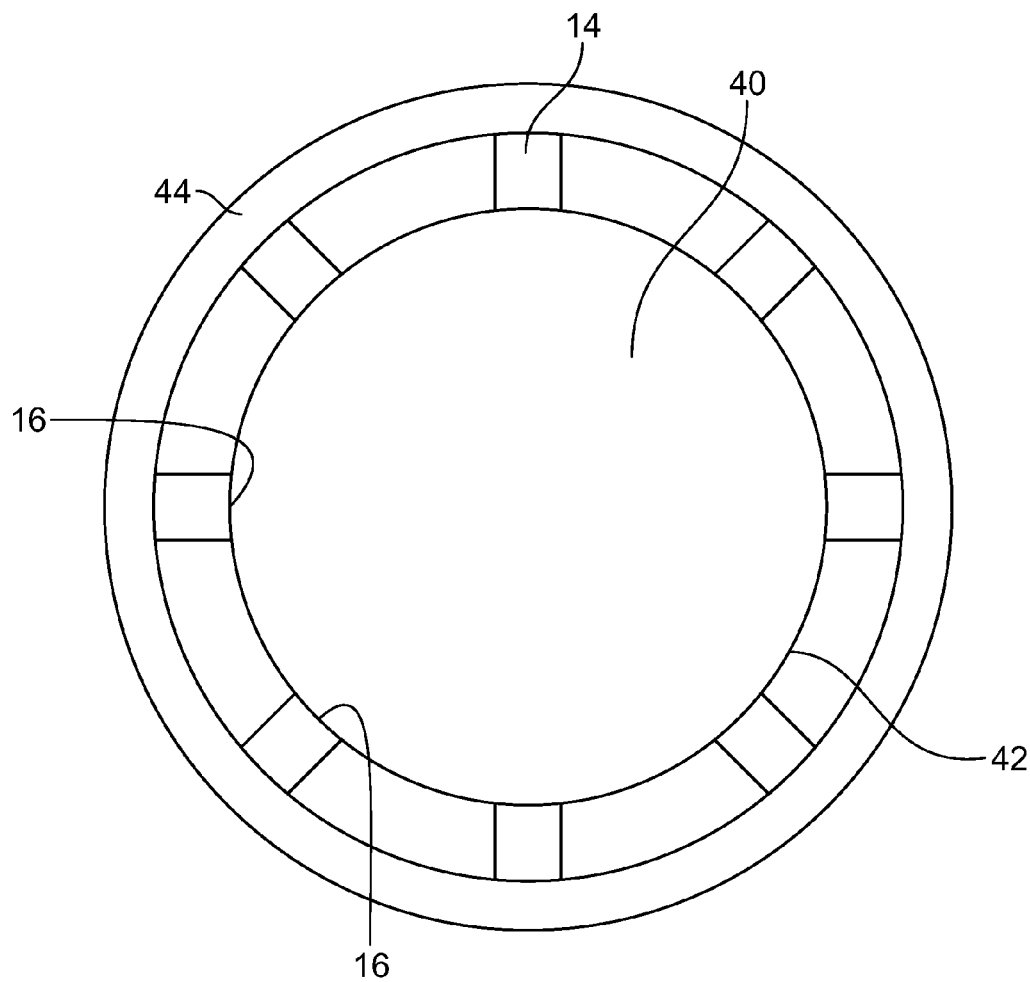
FIG. 5 shows a stent loaded on an inflatable or expandable mandrel or balloon, with a tube placed around the stent.

FIG. 5 illustrates another embodiment of a method for applying a coating to the inside surface of a stent without applying that coating to the outside surface of the stent. An expandable device 40, such as an inflatable or expandable mandrel or balloon, is provided with the coating material such that the coating material is deliverable from an outside surface 42 of the expandable device 40. The expandable device 40 may have a transfer film (which can be part of the expandable device) or a surface capable of carrying the desired coating material, in which case the coating material is placed on the surface of the expandable device 40. Additionally or alternatively, the coating material may be located within or deliverable to the expandable device 40, such that the coating material can be delivered from an outside surface 42 of the expandable device 40 to the stent 14. In a specific embodiment, a balloon 40 is used with a porous outer layer which becomes permeable and releases the coating upon reaching a specific pressure. The balloon 40 can be made, for example, of a PTFE semi-permeable membrane like those used for making filter membranes by companies like Millipore Corporation. The pore size may be on the order of 0.2 microns or any other suitable size, tailored to the specific requirements for efficient coating transfer. The balloon 40 may also be a dual layer balloon, like a balloon within a balloon, with the coating material within the balloon in the area between the two layers. The layers may be of different materials. For example, the inner balloon may be of a strong non-compliant or semi-compliant material such as PET while the outside layer can be of a compliant or even elastic material so that as pressure is increased the outer layer is stretched to open the pores in it to release the coating material.

The stent 14 is loaded on the expandable device 40 by being placed around the expandable device 40. Then, the expandable device 40 is expanded such that an outside surface 42 of the expandable device 40 (which could be a transfer film portion of the expandable device) contacts the inside surface 16 of the stent 14. Then, the coating material is transferred from the expandable device 40 to the inside surface 16 of the stent 14.

As shown in FIG. 5, to prevent the stent 14 from undesirably expanding, a tubular structure such as a tube or mesh 44 may be placed around the stent 14 to restrain expansion of the stent. The tube or mesh 44 may be made of metal, such as stainless steel, or any other suitably strong material. As described above, heat can be applied to facilitate the coating transfer.

Figure 7:
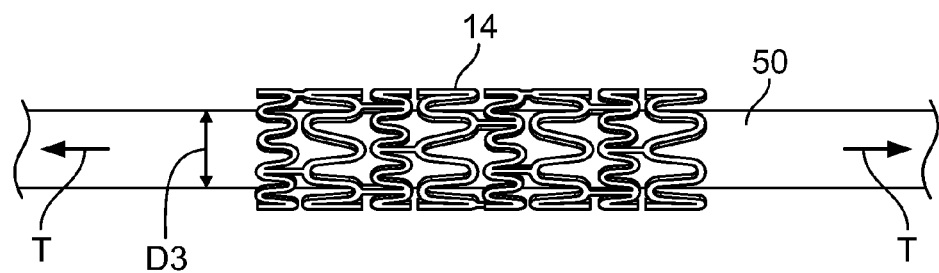
FIG. 7 shows a stent on an elongated material that reduces in diameter when placed under tensile force, with the elongated material being under tensile force.
Figure 8:
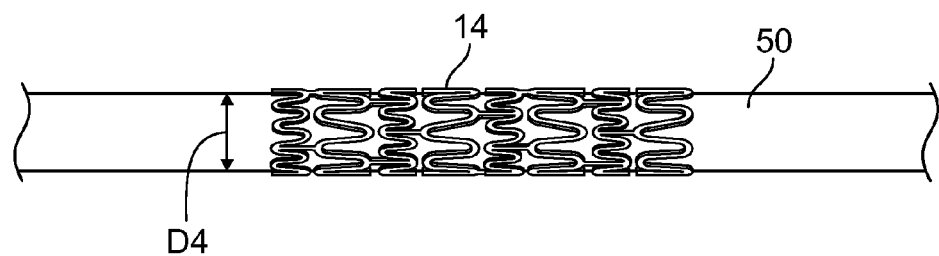
FIG. 8 shows the stent and elongated material of FIG. 7 with the tensile force released.

FIGS. 7 and 8 illustrate another embodiment of a method for applying a coating to the inside surface of a stent without applying that coating to the outside surface of the stent. An elongated material 50 that is capable of having its diameter reduced under the application of a tensile force, such as SUPERFLOSS™ or elastic beading, carries the desired coating material to be transferred to the inside surface of a stent 14. The coating material may be provided around the elongated material 50. As shown in FIG. 7, a tensile force T is applied to the elongated material 50 to stretch it, thereby reducing its diameter to a smaller diameter D3. In this condition, a stent 14 is loaded onto the elongated material 50, by being placed around the elongated material 50.

After the stent 14 is loaded, the tensile force applied to the elongated material 50 is released or reduced, allowing the diameter of the elongated member 50 to increase so that the coating material contacts the inside surface of the stent 14. As shown in FIG. 8, the diameter of the elongated material 50 expands to a larger diameter D4. In this condition, the coating material on the outside of the elongated material 50 contacts the inside surface of the stent 14. The coating material is transferred from the elongated material 50 to the inside surface of the stent 14, which may be aided by moving the elongated material 50 or the stent 14 from side to side. As described above, heat can be applied to facilitate the coating transfer.

The stent used in the present invention may be of any suitable type. This stent may be self-expanding, mechanically expandable, or a hybrid stent which may have both self-expanding and mechanically expandable characteristics. The stent may be made in a wide variety of designs and configurations, and may be made from a variety of materials including plastics and metals.

Various methods may be employed for delivery and implantation of the stent. For instance, a self-expanding stent may be positioned at the distal end of a catheter around a core lumen. Self-expanding stents may be typically held in an unexpanded state during delivery using a variety of methods including sheaths or sleeves which cover all or a portion of the stent. When the stent is in its desired location of the targeted vessel the sheath or sleeve is retracted to expose the stent which then self-expands upon retraction.

Another method includes mounting a mechanically expandable stent on an expandable member, such as a dilatation balloon provided on the distal end of an intravascular catheter, advancing the catheter through a patient's vasculature to the desired location within the patient's body lumen, and inflating the balloon on the catheter to expand the stent into a permanent expanded condition.

One method of inflating the balloon includes the use of inflation fluid. The expandable member is then deflated and the catheter removed from the body lumen, leaving the stent in the vessel to hold the vessel open.

The coating, in accord with the embodiments of the present invention, may comprise a polymeric and or therapeutic agent formed, for example, by admixing a drug agent with a liquid polymer, in the absence of a solvent, to form a liquid polymer/drug agent mixture. A suitable list of drugs and/or polymer combinations is listed below. The term "therapeutic agent" as used herein includes one or more "therapeutic agents" or "drugs". The terms "therapeutic agents" or "drugs" can be used interchangeably herein and include pharmaceutically active compounds, nucleic acids with and without carrier vectors such as lipids, compacting agents (such as histones), viruses (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor ∀ and ∃, platelet-derived endothelial growth factor, platelet-derived growth factor, tumor necrosis factor ∀, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

As stated above, coatings used with the exemplary embodiments of the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

In accord with the embodiments, the polymer used to coat the medical device is provided in the form of a coating on an expandable portion of a medical device. After applying the drug solution to the polymer and evaporating the volatile solvent from the polymer, the medical device may be inserted into a body lumen where it is positioned to a target location. In the case of a balloon catheter, the expandable portion of the catheter may be subsequently expanded to bring the drug-impregnated polymer coating into contact with the lumen wall. The drug is released from the polymer as it slowly dissolves into the aqueous bodily fluids and diffuses out of the polymer. This enables administration of the drug to be site-specific, limiting the exposure of the rest of the body to the drug.

The polymer used in the exemplary embodiments of the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method of applying a coating material to a stent, comprising:
   (i) providing a generally tubular stent having an inside surface and an outside surface;
   (ii) providing a coating material; and
   (iii) applying the coating material to the inside surface of the stent without applying the coating material to the outside surface of the stent, wherein the step of applying the coating material to the inside surface of the stent without applying the coating material to the outside surface of the stent includes the steps of:
      (a) providing a mandrel having a diameter less than an interior diameter of the stent;
      (b) providing the coating material around the mandrel;
      (c) placing the stent around the mandrel in the area of the coating material;
      (d) crimping the stent by reducing its diameter so that the inside surface of the stent contacts the coating material; and
      (e) transferring the coating material to the inside surface of the stent.

2. A method as recited in claim 1, further comprising applying heat to facilitate the transferring of the coating material to the inside surface of the stent.

3. A method as recited in claim 1, wherein the step of providing the coating material around the mandrel includes:
   providing a transfer film with the coating material on the transfer film; and
   placing the transfer film around the mandrel.

4. A method as recited in claim 1, wherein the step of providing the coating material around the mandrel includes providing the coating material directly on the mandrel.

5. A method as recited in claim 1, wherein the coating material comprises an endothelial cell growth promoter.

6. A method of applying a coating material to a stent, comprising:
   (i) providing a generally tubular stent having an inside surface and an outside surface;
   (ii) providing a coating material; and
   (iii) applying the coating material to the inside surface of the stent without applying the coating material to the outside surface of the stent, wherein the step of applying the coating material to the inside surface of the stent without applying the coating material to the outside surface of the stent includes the steps of:
      (a) providing an expandable device;
      (b) providing the expandable device with the coating material such that the coating material is deliverable from an outside surface of the expandable device;
      (c) placing the stent around the expandable device;
      (d) expanding the expandable device such that the outside surface of the expandable device contacts the inside surface of the stent; and
      (e) transferring the coating material from the expandable device to the inside surface of the stent;
   wherein the expandable device is an expanding mandrel.

7. A method as recited in claim 6, wherein the step of providing the expandable device with the coating material includes placing the coating material within the expandable device.

8. A method as recited in claim 7, wherein the outer surface of the expandable device includes pores for releasing the coating material.

9. A method as recited in claim 8, wherein the pores open when the expandable device reaches a desired condition.

10. A method as recited in claim 6, wherein the step of providing the expandable device with the coating material includes placing the coating material on a surface of the expandable device.

11. A method as recited in claim 6, further comprising providing a tubular structure around the outside of the stent to restrain expansion of the stent.

12. A method as recited in claim 6, wherein the coating material comprises an endothelial cell growth promoter.

13. A method of applying a coating material to a stent, comprising:
   (i) providing a generally tubular stent having an inside surface and an outside surface;
   (ii) providing a coating material; and
   (iii) applying the coating material to the inside surface of the stent without applying the coating material to the outside surface of the stent, wherein the step of applying the coating material to the inside surface of the stent without applying the coating material to the outside surface of the stent includes the steps of:
      (a) providing an elongated material that is capable of having its diameter reduced under the application of a tensile force;
      (b) providing the coating material around the elongated material;
      (c) applying a tensile force to the elongated material to reduce its diameter;
      (d) placing the stent around the elongated material;
      (e) reducing or releasing the tensile force applied to the elongated material, thereby allowing the diameter of the elongated member to increase so that the coating material contacts the inside surface of the stent; and
      (f) transferring the coating material from the elongated material to the inside surface of the stent.

14. A method as recited in claim 13, further comprising applying heat to facilitate the step of applying the coating material to the inside surface of the stent.

15. A method as recited in claim 13, wherein the coating material comprises an endothelial cell growth promoter.

* * * * *